(12) United States Patent
Lindenroth et al.

(10) Patent No.: US 11,737,729 B2
(45) Date of Patent: Aug. 29, 2023

(54) CONTROLLED BENDING FOR CATHETERS

(71) Applicant: Siemens Healthcare GmbH, Erlangen (DE)

(72) Inventors: Lukas Lindenroth, London (GB); Erin Girard, Madison, CT (US); Rodolfo Finocchi, Cambridge, MA (US); Young-Ho Kim, West Windsor, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1007 days.

(21) Appl. No.: 16/544,116

(22) Filed: Aug. 19, 2019

(65) Prior Publication Data

US 2020/0061339 A1 Feb. 27, 2020

Related U.S. Application Data

(60) Provisional application No. 62/720,532, filed on Aug. 21, 2018.

(51) Int. Cl.
*A61B 8/00* (2006.01)
*A61B 8/08* (2006.01)
*A61M 25/01* (2006.01)
*A61M 25/00* (2006.01)
*A61B 8/12* (2006.01)

(52) U.S. Cl.
CPC ............ *A61B 8/445* (2013.01); *A61B 8/0883* (2013.01); *A61B 8/4254* (2013.01); *A61B 8/4466* (2013.01); *A61B 8/12* (2013.01); *A61M 25/0054* (2013.01); *A61M 25/0136* (2013.01); *A61M 25/0147* (2013.01); *A61M 25/0152* (2013.01)

(58) Field of Classification Search
CPC ..... A61B 8/445; A61B 8/0883; A61B 8/4254; A61B 8/4466; A61B 8/12; A61M 25/0054; A61M 25/0136; A61M 25/0147; A61M 25/0152
See application file for complete search history.

(56) References Cited

U.S. PATENT DOCUMENTS

| | | | |
|---|---|---|---|
| 2006/0122514 A1* | 6/2006 | Byrd ...................... | A61B 8/463 600/466 |
| 2007/0167813 A1* | 7/2007 | Lee ....................... | A61B 8/4488 600/459 |
| 2009/0005679 A1* | 1/2009 | Dala-Krishna ...... | A61B 8/5284 600/437 |

(Continued)

OTHER PUBLICATIONS

Corindus "Corpath GRX Precision Vascular Robotics" retrieved at https://www.corindus.com/corpath-grx/how-it-works accessed Aug. 14, 2019. pp. 1-5.

(Continued)

*Primary Examiner* — Christopher Koharski
*Assistant Examiner* — Taylor Deutsch

(57) ABSTRACT

For rotation compensation in a catheter, a rotation sensor senses rotation of the handle or catheter. Motors are controlled to change the bend in response to sensed rotation. As the tip rotates due to handle rotation, the motors change the bend to maintain the bend and tip position relative to the patient. This steering in the patient reference frame may be more intuitive, easier to learn, and allow rotation to change an imaging field of view without moving the bending planes.

17 Claims, 4 Drawing Sheets

(56) References Cited

U.S. PATENT DOCUMENTS

| | | | | |
|---|---|---|---|---|
| 2010/0179426 A1* | 7/2010 | Davies | ................. | A61B 8/4483 |
| | | | | 600/439 |
| 2011/0144576 A1 | 6/2011 | Rothe | | |
| 2011/0263983 A1* | 10/2011 | Peszynski | .............. | A61B 8/445 |
| | | | | 600/443 |
| 2012/0071895 A1* | 3/2012 | Stabler | ................... | A61B 34/20 |
| | | | | 606/130 |
| 2013/0102960 A1* | 4/2013 | Miyoshi | ............ | A61M 25/0136 |
| | | | | 604/95.04 |

OTHER PUBLICATIONS

Dicardiology "FDA Clears Hansen Magellan Robotic System for Peripheral Vascular Interventions" retrieved at https://vww.dicardiology.com/product/fda-clears-hansen-magellan-robotic-system-peripheral-vascular-interventionsDated Jun. 5, 2012. pp. 1-3.

Loschak, Paul M., et al. "A 4-DOF robot for positioning ultrasound imaging catheters." ASME 2015 International Design Engineering Technical Conferences and Computers and Information in Engineering Conference. American Society of Mechanical Engineers, 2015. pp. 1-10.

Medgadget "Sensei X Robotic Catheter System for Electrophysiology Procedures" retrieved at https://www.medgadget.com/2009/09/sensei_x_robotic_catheter_system_for_electrophysiology_procedures.html Dated Sep. 18, 2009. pp. 1-4.

\* cited by examiner

CONTROLLED BENDING FOR CATHETERS

RELATED APPLICATION

The present patent document claims the benefit of the filing date under 35 U.S.C. § 119(e) of Provisional U.S. Patent Application Ser. No. 62/720,532, filed Aug. 21, 2018, which is hereby incorporated by reference.

BACKGROUND

The present embodiments relate to steering catheters. Cardiac catheters are commonly steered in 4 degrees of freedom. The catheter may be bent along two principal axes of the catheter by turning two independent knobs placed on the catheter's handle. The knobs are often labelled "anterior-posterior" for one bending plane and "left-right" for the perpendicular bending plane, both with respect to the catheter reference frame. In addition to the bending, the clinician may translate and rotate the catheter tip along and around its longitudinal axis by translating and rotating the catheter handle, respectively. Rotating the catheter tip is particularly important for intra-cardiac echocardiography catheters as the imaging transducer is commonly located on one side of the catheter tip and can therefore only acquire images in this particular direction unless rotated. The tip is rotated to image a different part of the patient. Rotating the handle, however, causes the two knobs and the two bending planes to rotate correspondingly. The operator then has to rely on image feedback to accurately re-establish the bending directions with respect to the patient's anatomy.

A mechanical catheter handle, proposed in U.S. Published Patent Application No. 2011/0144576A1, separates a rotational mechanism and user input joystick. The joystick replaces the knobs and remains in place when the catheter handle is rotated. While this mechanism resolves the issue of decoupling the rotation of the catheter handle from the bending controls, rotation still moves the bending planes.

SUMMARY

By way of introduction, the preferred embodiments described below include methods, systems, and catheters for rotation compensation. A rotation sensor senses rotation of the handle or catheter. Motors are controlled to change the bend in response to sensed rotation. As the tip rotates due to handle rotation, the motors change the bend to maintain the bend and tip position relative to the patient. This steering in the patient reference frame may be more intuitive, easier to learn, and allow rotation to change an imaging field of view without moving the bending planes.

In a first aspect, a medical ultrasound system is provided for intra-cardiac echocardiography. An intra-cardiac echocardiography catheter has a tip, a handle, steering wires, and an ultrasound transducer array. A plurality of motors connects to the steering wires of the intra-cardiac echocardiography catheter. A rotation sensor is positioned to sense rotation of the handle. A controller is configured to maintain a position of the tip relative to a patient during rotation of the handle by actuation of one or more of the motors in response to the sensed rotation.

In one embodiment, the ultrasound transducer array is a one-dimensional array of transducer elements for scanning a patient within a field of view. The one-dimensional array is on a distal end of the intra-cardiac echocardiography catheter for insertion within the patient.

According to another embodiment, the steering wires control a bend at a distal end of the intra-cardiac echocardiography catheter. The controller is configured to maintain the position of the tip by altering the bend during the rotation. The motors may be of various types, such as linear motors. Various types of rotation sensors may be used, such as an inertial measurement unit.

In another embodiment, the controller is configured to establish a patient frame of reference based on registration of a catheter frame of reference with a medical image. The position is maintained as part of steering in the patient frame of reference.

In yet another embodiment, the tip rotates as the handle rotates. The controller is configured to alter a bend in the intra-cardiac echocardiography catheter to maintain the position during the rotation. The rotation causes the ultrasound transducer array and a corresponding field of view to rotate while the position is maintained.

According to another embodiment, one or more input sensors are on the handle. The input sensors are configured for steering the intra-cardiac echocardiography catheter from user input. The steering is with respect to a patient frame of reference different from a catheter frame of reference for the intra-cardiac echocardiography catheter.

In other embodiments, an ultrasound scanner or scanner components are provided. For example, a beamformer is configured to scan from the ultrasound transducer array.

In a second aspect, a method is provided for controlled bending in a catheter. A sensor senses rotation of the catheter along a longitudinal axis of the catheter. A controller alters a bend in the catheter so that a portion of the catheter separated from a handle by the bend remains at a location relative to a patient. The altering of the bend is based on the sensed rotation from the sensor.

In further embodiments, an inertial measurement unit in or on a handle of the catheter senses; and/or one or more motors in a handle of the catheter connect to steering wires of the catheter for altering.

In one embodiment, the altering includes maintaining an angle of the bend along the catheter during the rotation and maintaining a location of the bend relative to the patient during the rotation. In other embodiments, the portion includes an acoustic imaging array. The acoustic imaging array is rotated with the rotation, the bend is altered so that the portion remains at a location while also rotating the acoustic imaging array.

In a third aspect, a method is provided for steering a catheter. The catheter is inserted into a patient. A controller and motor steer the catheter with respect to a patient reference frame different than a catheter reference frame of the catheter.

In a further embodiment, the steering with respect to the patient reference frame includes maintaining bending planes of the catheter in positions relative to the patient during rotation of the catheter about a longitudinal axis of the catheter.

In an embodiment with an imaging array, a field of view is ultrasonically scanned with a transducer in the catheter. The steering maintains the transducer at a same location relative to the patient while rotating the transducer and field of view at the location.

In another further embodiment, a rotation of a handle of the catheter is sensed. The steering includes changing a bend in the catheter in response to the sensed rotation. Various sensors may be used, such as sensing with an inertial measurement unit.

The present invention is defined by the following claims, and nothing in this section should be taken as a limitation on those claims. Features of one aspect or type of claim (e.g., method or system) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Rotation compensation is provided for catheter systems. The combination of an active handheld catheter steering system with a sensor for rotation compensation provides for automated steering of the catheter tip in the patient reference frame. An active, handheld catheter system adaptively compensates for orientation changes in the catheter handle by measuring absolute orientation using an inertial orientation measurement unit or other sensor and by adjusting the tip bending accordingly. The bending of the catheter tip is with respect to the patient's reference frame or anatomy rather than the catheter reference frame, simplifying the catheter steering for the operator. Steering in the patient reference frame may reduce training costs and/or procedure time for clinical interventions.

For an intra-cardiac echocardiography (ICE) catheter, the field of view of the transducer at the tip or distal end of the catheter may be rotated while maintaining the transducer in a position relative to the patient. The manipulation of the catheter and imaging plane is simplified by steering in the patient frame of reference.

Figure 1:
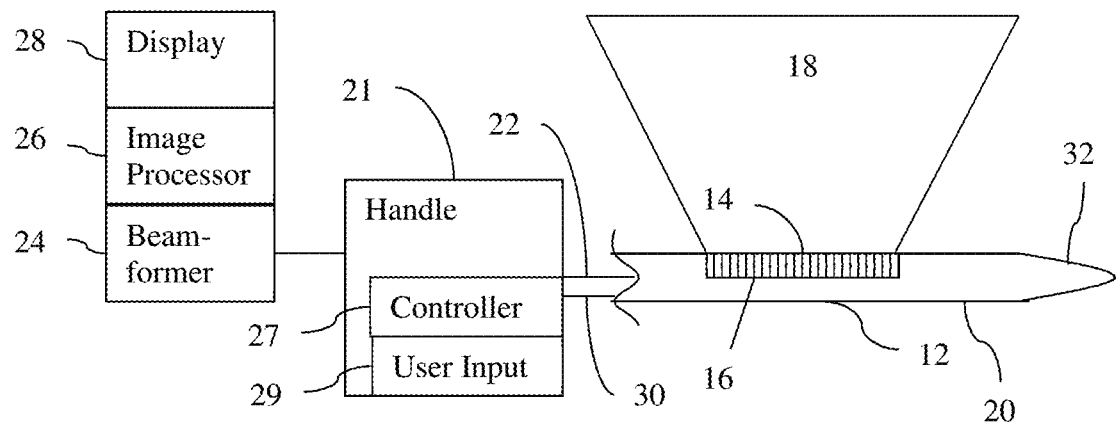
FIG. 1 is a block diagram of one embodiment of a medical ultrasound system for rotation compensation in an imaging catheter.
Figure 1:
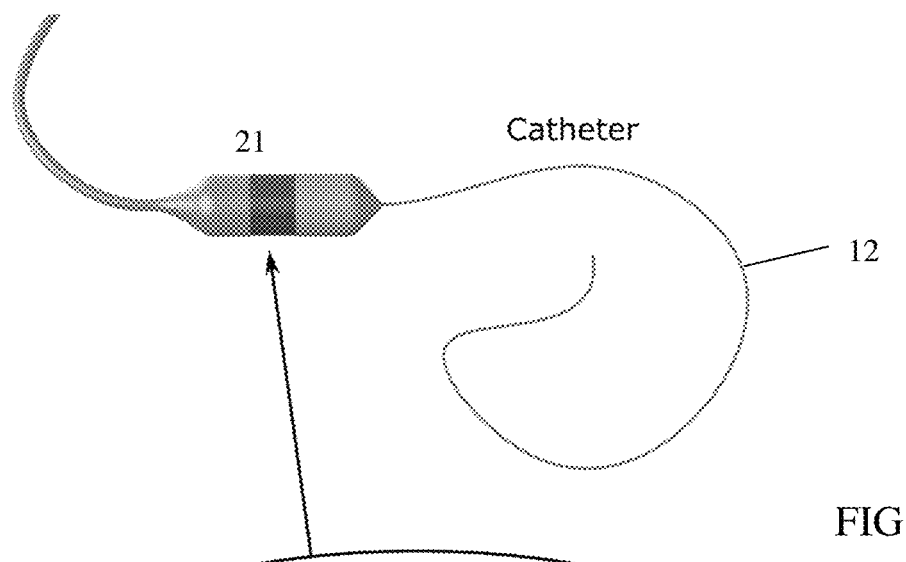

FIG. 1 shows a medical ultrasound system for intra-cardiac echocardiography. In other embodiments, other types of catheters are used. For example, an ablation catheter is used. Alternatively, transesophageal echocardiogram or transthoracic echocardiogram probes are used. The system with the corresponding catheter uses patient anatomy-centric steering. During rotation of the catheter, one or more parts of the catheter are maintained in a position relative to the patient even where the steering establishes a bend. The bend is altered during rotation to maintain position of a distal part of the catheter.

The medical ultrasound system includes the intra-cardiac echocardiography catheter 12, a beamformer 24, an image processor 26, and a display 28. Additional, different, or fewer components may be provided. For example, the system includes the array 14 in a catheter 12 without the beamformer 24, image processor 26, and/or display 28. These imaging electronics may be in a separate ultrasound imaging system. The catheter 12 releasably connects with the imaging system. As another example, the system is for ablation or other purpose than ultrasound. An ablation or other type of catheter is used without the beamformer 24, image processor 26, and/or display 28.

The intra-cardiac echocardiography catheter 12 includes an array 14 of elements 16 for imaging within a housing 20 having a tip 32, electrical conductors 22, steering wires 30, and a handle 21. Additional, different, or fewer components may be provided, such as radio opaque markers, ablation electrodes, lens, needle guide, or ports.

The housing 20 is PEBAX, nylon, polymer, or other flexible material. The housing 20 is formed around the array 14. In other embodiments, the housing 20 includes one or more windows or openings through which the array 14 is exposed. The housing 20 is configured for insertion into a circulatory system of a patient. For example, the distal tip 32 of the catheter 12 includes a more flexible portion covered by the housing 20 for moving through the circulatory system. Steering wires 30 connected to the housing 20 or parts within the housing 20 are configured to guide the housing 20 within the circulatory system.

The array 14 has a plurality of elements 16, backing block, electrodes, and a matching layer. Additional, different, or fewer components may be provided. For example, two, three, or more matching layers are used. The backing block material absorbs and/or reflects acoustic energy. The matching layers provide a more gradual transition between acoustic impedance, minimizing reflection from the boundary between the transducer and the patient. The electrodes interact with the elements to transduce between acoustic and electrical energy. The variation of potential or distance between electrodes across an element 16 causes electrical signal or acoustic energy generation, respectively. In one embodiment, a flex circuit connect from the elements 16 to a bundle of conductors 22 that carry the signals between the beamformer 24 and the array 14.

Any number of elements 16 may be provided, such as 64 elements. 128 or other number of elements 16 may allow for larger apertures and/or a greater number of apertures. The elements 16 are adjacent to each other, such as having substantially wavelength or less spacing between the centers of adjacent elements 16. For example, the elements 16 have half wavelength spacing with kerfs acoustically separating each element 16. Sparse arrays 14 with greater spacing between elements 16 may be used.

The elements 16 are positioned along an azimuth axis of the array 14 (longitudinal axis of the catheter 12). For a one-dimensional array 14, the elements 16 are in a single row along the azimuth axis. The array 14 may be linear or curved linear. For use in a catheter, the azimuth axis is along the longitudinal axis of the catheter 12 but may be offset from the axis or centered along the axis. The array 14 of the elements 16 is of any length, such as 7 mm, 14 mm, or 28 mm. Multi-dimensional arrays 14 may be used, such as 1.25, 1.5, 1.75 or 2D arrays. In one embodiment for volume imaging from a thin and long catheter, the array 14 twists about the longitudinal or azimuth axis of the array or an axis spaced from the center of the array. Different elements 16 or groups of elements 16 face in different directions. For example, the twist follows a helical pattern. By walking an aperture along the array 14, different scan planes spaced or fanned apart in elevation are defined and used for scanning. This allows scanning of a volume with the linear array.

The array 14 is positioned within the catheter 12. The array 14 may fit within 10 French, 3.33 mm, 12.5 French, or another diameter catheter 12. The array 14 is at a distal end or tip 32 of the catheter 12, such as being within 20 mm of an end of the tip 32 or a beginning of a flexible tip portion. The array 14 may have any position within the catheter 12 that results in the array 14 being within the patient during use of the catheter 12 for imaging.

The transducer array 14 is used for ultrasound imaging. The images assist in diagnosis, catheter guidance, needle guidance, ablation guidance, placement, and/or needle puncture. The side of the elements 16 covered by the matching layer, closer to the region to be scanned and/or opposite the backing block, is the emitting face of the array 14. Acoustic energy is transmitted from and received at the emitting face of the array 14. The angle of acoustic energy relative to the emitting face affects the sensitivity of the elements 16 to the energy. The elements 16 are more sensitive to the energy at normal incidence to the elements 16. The array 14 scans in a field of view 18 in a plane perpendicular to the emitting face. The array 14 is used to scan in the field of view 18 or region of desired sensitivity to any desired depth. This field of view 18 of the array 14 has any format for the corresponding scan pattern, such as Vector®, sector, or linear. The patient within the field of view 18 may be imaged using the array 14.

Electrical conductors 22 connect the elements 16 of the array 14 to the beamformer 24. The conductors 22 are cables, coaxial cables, traces on flexible circuit material, wires, continuation of the flex circuits, wire jumpers, combinations thereof, and/or other now known or later developed conductor. One conductor 22 is provided for each element 16. Alternatively, fewer conductors 22 than elements 16 may be used, such as for switched apertures, partial beamforming, or multiplexing. The conductors 22 are separately addressable by the beamformer 24. Each element 16 may be selectively used for a given aperture and associated electronic steering. Alternatively, some elements 16 are useable with only a subset of possible apertures.

In other embodiments, other types of catheters 12 are used. The catheter 12 may be directional. For example, the imaging catheter 12 of FIG. 1 has a field of view 18 from one side of the catheter 12. As another example, an ablation electrode is positioned on one side of the catheter 12. Ports, needle guides, or other structure may be on one side or not uniformly spaced about the circumference of the catheter 12. The catheter 12 may not be directional, such as having an ablation electrode around the circumference and/or at the tip.

Figure 3:
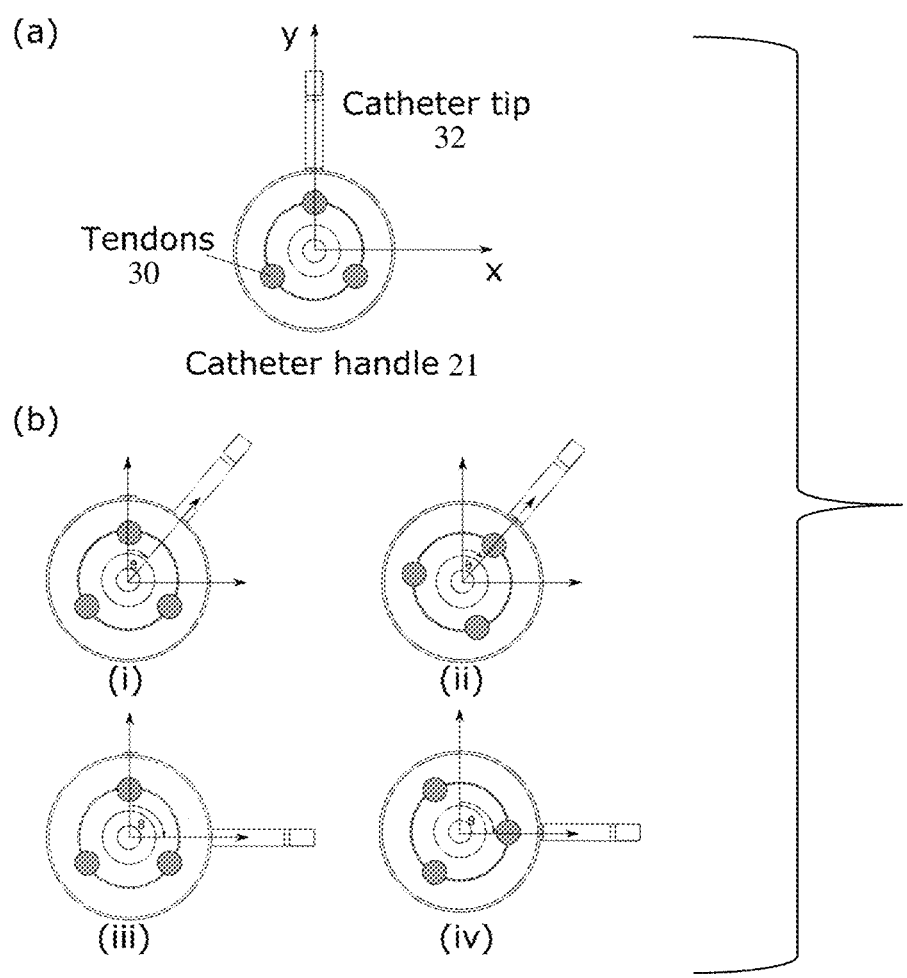
FIG. 3 illustrates two approaches to alter a bend in a catheter.
Figure 4:
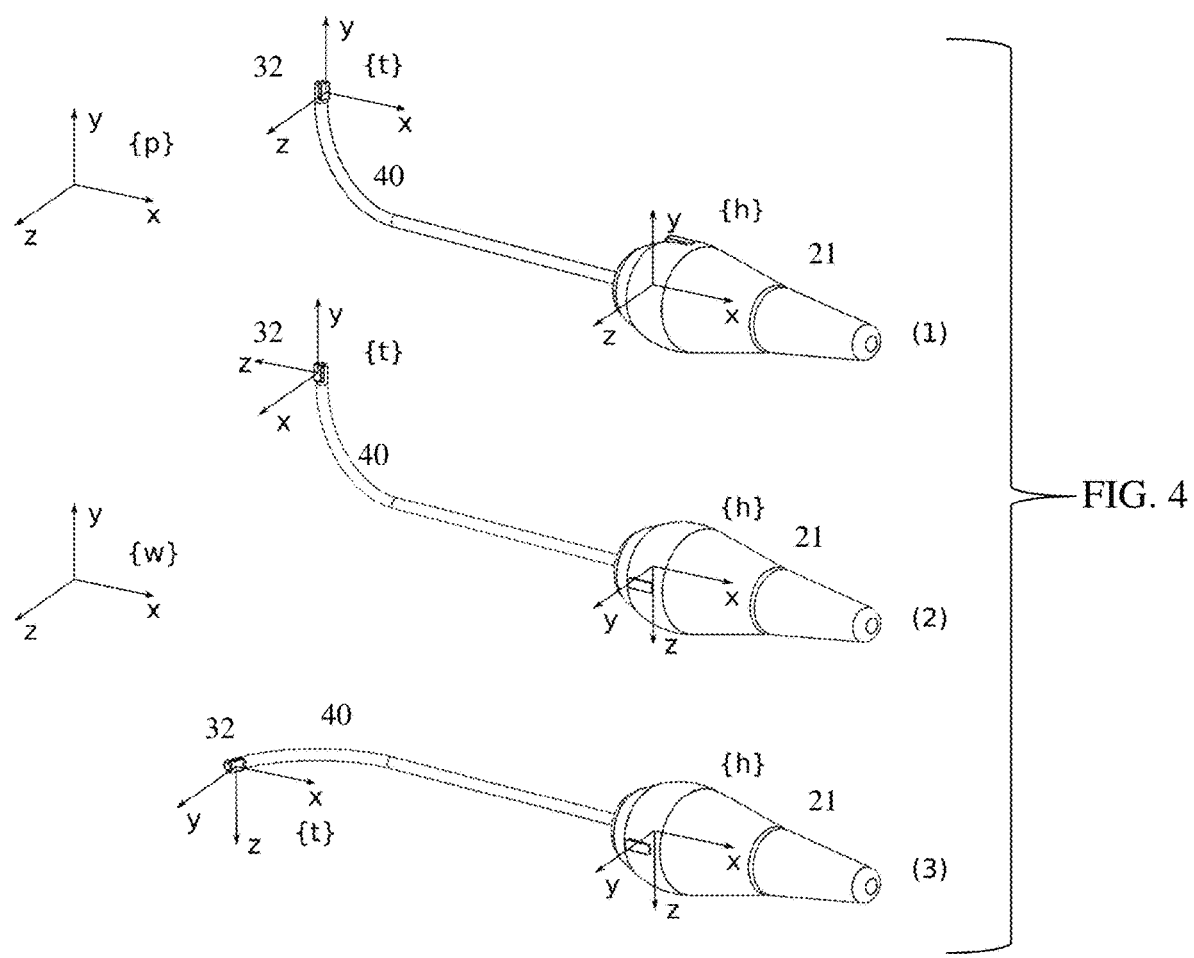
FIG. 4 illustrates an example of changing bending planes with rotation and an example of maintaining bending planes during rotation.

The steering wires 30 are cables, tendons, or other structure for transferring push and pull force from the handle 21 to a portion of the catheter 12 within a patient, such as to the distal end or the tip 32. Any material may be used, such as plastic, fiberglass, or metal. Any number of steering wires 30 may be used, such as three or four wires. As shown in FIG. 3, three steering wires 30 offset from the center in an equal spacing may be used to steer along two perpendicular planes. The relative force between the steering wires 30 causes the catheter 12 to bend. For example, FIG. 4 shows the steering wires 30 causing a 90-degree bend 40. Other degrees of bending may be provided. Any now known or later developed arrangement of steering wires 30 may be used.

The steering wires 30 control the bend 40 at a distal end of the catheter 12. The bend 40 may be at a portion of the catheter 12 adjacent to the distal end or tip 32, such as providing for the array 14 to be spaced from the handle 21 by the bend 40.

The handle 21 includes a housing, motors 25, a controller 27, and user input 29. Additional, different, or fewer components may be used. For example, the motors 25, controller 27, and/or user input 29 are separated from the handle 21.

The handle 21 is shaped and sized for handheld guidance or use of the catheter 12. For example, the handle 21 is cylindrical with grips to be used by one hand of a surgeon.

The motors 25 are linear motors, servo motors, rotational motors, or other electric, pneumatic, or hydraulic motors for applying push or pull force to the steering wires 30. A separate motor 25 is provided for each steering wire 30. Alternatively, gearing, clutch, and/or transmission is used to apply force from one motor 25 to multiple steering wires 30.

The motors 25 automate the catheter 12 bending. To actuate the bending of the catheter 12 by tendons or steering wires 30 running along the catheter 12, the motors 25 apply tendon pulling or pushing forces. This allows the operator to induce catheter 12 bending by only adjusting the user input 29 without having to apply the forces themselves.

FIG. 3 shows one embodiment of steering by the motors 25 using the steering wires 30 and by manual rotation. In FIG. 3(a), the steering wire 30 in the top of the handle 21 applies pulling force and/or the other two steering wires 30 apply pushing force. This causes the catheter bend, placing the catheter tip 32 along the Y-axis. FIG. 3(b) shows two ways to change the position of the bend and/or catheter tip 32. The entire handle 21 may be rotated by 45 degrees (FIG. 3(b)(ii)), 90 degrees (FIG. 3(b)(iv)), or another amount, which rotates the bending plane. Alternatively, the relative push and/or pull forces on the steering wires 30 are changed, which rotates the bending plane. For 45-degree alteration of the bend (FIG. 3(b)(i)), two steering wires 30 pull while one steering wire pushes. Since the 45-degree angle is not exactly between two steering wires 30, the two pulling steering wires 30 pull by different amounts. The relative amounts are different to achieve the 90-degree alteration (FIG. 3(b)(iii)). Any combination of relative forces may be used. The same shift in the bend plane may be provided by either rotating the handle 21 or by changing the forces on the steering wires 30.

By using the motors 25, the same steering may be provided as rotating the handle 21, but without rotating the handle 21. The bend in the catheter frame of reference is altered by the motors 25. This alteration changes the position of the catheter tip 32 and corresponding bend relative to the patient frame of reference.

The motors 25 may be used to change the bend in the catheter frame of reference to maintain the position of the bend in the patient frame of reference. The steering is used to avoid altering the bending plane. For example, the user rotates the handle 21. Instead of the rotation rotating the bend 40 and the catheter tip 32 as shown in FIGS. 3(b)(ii) and (iv), the motors 25 change the relative forces on the steering wires 30 to keep the catheter tip 32 in the same position (e.g., catheter tip 32 stays in the Y-axis of the patient frame of reference). The planes defining the bend 40 may be maintained or fixed relative to the patient.

FIG. 4 shows an example. FIG. 4(1) shows a bend 40 with the handle 21 at one orientation, positioning the tip 32 at a location. {w} is a fixed world frame and {p} is the patient frame. {h} expresses the pose of the catheter handle 21 within the world frame, and {t} is the tip transducer frame. If, from an initial orientation of FIG. 4(1), {h} (handle 21) is rotated about its x-axis by an operator, the tip 32 of the catheter would move in space and rotate about the local {h} reference frame, which would result in a new pose of FIG. 4(3) where the plane of bending is rotated with the handle 21. If the motors 25 instead compensate for the rotation, the tip 32 may be maintained at a same location in the world frame {w} and the patient frame {p} as shown in FIG. 4(2). The bend 40 is altered to maintain the position of the tip 32. Rotating the handle 21 in the handle frame {h} results in a pure rotation of {t} about its pose with respect to the world. The tip 32 is rotated with respect to a known patient reference frame {p} while the rotation is compensated for by altering the bend 40.

Referring again to FIG. 1, the user inputs 29 are devices, such as sensors, for receiving user input. For example, the user inputs 29 are electrical sensors, such as potentiometers or capacitive sensors, connected with rockers, knobs, dials, touch pads, joysticks, or other devices for steering. The user activates one or more user inputs 29 on the handle 21 for manually controlling the bend 40.

The user inputs 29 receive user input of steering control. The controller 27 maps those inputs into steering with respect to the patient frame of reference. Without rotation of the handle 21, an input may be received by the user inputs 29 to bend more or less in a same plane or to alter the plane in which the bend occurs relative to the catheter and patient frames of reference. With rotation of the handle 21 and without input on the user input 29, the bend 40 may be maintained in a same plane despite the rotation. In alternative embodiments, the rotation of the tip 32 of the catheter 12 is performed by a motor in the handle 21 without rotation of an exterior of the handle 21. The user input 29 is used to control the rotation performed by a motor.

For manual rotation of the handle 21, a rotation sensor 23 senses the rotation of the handle 21. The rotation sensor 23 is in or on the handle 21 for sensing the rotation of the handle 21 by the user.

Figure 2:
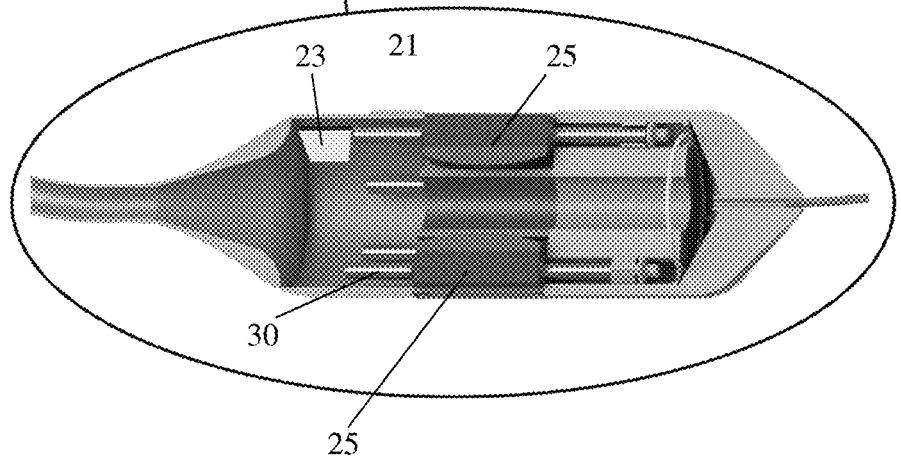
FIG. 2 illustrates one embodiment of a catheter with a handle.

Any sensor may be used. In the embodiment shown in FIG. 2, an inertial measurement unit is provided as the rotation sensor 23. In other embodiments, the user input 29 receives user input to rotate, providing sensing of the rotation. In yet other embodiments, a camera or imager with or without fiducials in or on the handle 21 is used to sense rotation. The camera or imager is spaced from the handle 21 to view the handle 21.

Referring to FIG. 4, the rotation compensation of the bend 40 maintains the position of tip 32 in the patient frame of reference. The position may not be maintained exactly due to rotation sensor tolerance, control tolerance, patient movement, and/or translational movement. The compensation maintains by attempting to keep the bend 40 in the same plane within the patient frame of reference, such as with +/−10 degrees.

During rotation of the catheter 12, the tip 32 rotates while the position is maintained. This rotation changes the field of view of the array 14, allowing imaging of other parts of the patient around the location. The user rotates the handle 21 or causes rotation of the catheter 12 to scan other planes or regions around the current location of the tip 32. The motors 25 are automatically controlled to alter the bend 40 to maintain the position in the patient frame of reference while the tip 32 rotates. The orientation of the tip 32 changes while the location or position is maintained.

The controller 27 is a processor, application specific integrated circuit, integrated circuit, digital signal processor, field programmable gate array, or other control device for controlling the motors 25. The controller 27 is configured by design, hardware, and/or software to steer in the patient frame of reference, such as to maintain the position of the tip 32 by altering the bend 40 during the rotation.

The controller 27 receives signals from the rotation sensor 23. The magnitude of rotation, rate of rotation, and/or absolute angle is translated to control signals for the motors 25 to change or alter the bend to maintain the position of the bend 40 and/or tip 32 relative to the patient during the rotation. The controller 27 actuates one or more motors 25 to change the amount of force applied to the steering wires 30, altering the steering to change the bend 40 to account for rotation. The bending plane relative to the catheter is kept in a same position for handle rotations using the orientation measurement of the catheter handle 21. The control allows for the orientation of the catheter 12 bending planes to be expressed with respect to a fixed world coordinate system. If the patient is registered within the world coordinate frame, or a registration is approximated according to the positioning of the patient, the bending of the catheter tip 32 may therefore be expressed with respect to the patient's anatomy.

For the intra-cardiac echocardiography catheter 12 to maintain the position during the rotation, the controller 27 controls the motors 25. As a result, the rotation causes the ultrasound transducer array 14 and a corresponding field of view 18 to rotate while the position is maintained. This compensation allows the user to rotate the view plane or field of view 18 without affecting the position of the catheter tip 32. Active orientation by the controller 27 accounts for the rotation.

The controller 27 establishes the patient frame of reference based on an initial position of the handle with respect to rotation. The compensation compensates for any rotation from the initial angle. In a further embodiment, the patient frame of reference is based on a registration of the catheter frame of reference with a medical image. For example, an x-ray image (e.g., fluoroscope image) is taken of the patient with the catheter 12 within the patient. Data processing is applied to identify the location of the catheter with respect to the x-ray imager and the position of the patient with respect to the x-ray imager. The position of the catheter 12 with respect to the patient is determined by spatial transform of the coordinate systems. The patient is registered within the world coordinate frame or a registration is approximated according to the positioning of the patient. Once registered, the bending of the catheter may be expressed with respect to the patient's anatomy.

The array 14 connects to the beamformer 24. The beamformer 24 includes a plurality of channels for generating transmit waveforms and/or receiving signals. Relative delays and/or apodization focus the transmit waveforms or received signals for forming beams and setting a focal location. The beamformer 24 connects with the conductors 22 for applying waveforms for imaging with the array 14.

For imaging, the beamformer 24 selects an aperture including one, some, or all of the elements 16 of the array 14. Different apertures may be used at different times. The aperture is formed by using the elements 16 for transmit and/or receive operations using all or a sub-set of the elements 16. For scanning, the beamformer 24 electronically focuses along the azimuth direction. A plurality of scan lines using an aperture is scanned. During receive operations, the focus may vary as a function of depth (i.e., dynamic focusing). An elevation focus is provided by a lens and/or element sensitivity, or the array 14 is not focused in elevation. In alternative embodiments, the beamformer 24 connects with elevation spaced elements for at least partial electric focusing and/or steering in the elevation dimension.

The image processor 26 is a detector, filter, processor, application specific integrated circuit, field programmable gate array, digital signal processor, control processor, scan converter, three-dimensional image processor, graphics processing unit, analog circuit, digital circuit, or combinations thereof. The image processor 26 receives beamformed data and generates images on the display 28, which is a display screen. The images are associated with a two-dimensional scan. Alternatively or additionally, the images are three-dimensional representations. Data representing a volume is acquired by scanning. The image processor 26 renders an image from the data representing the volume.

Figure 5:
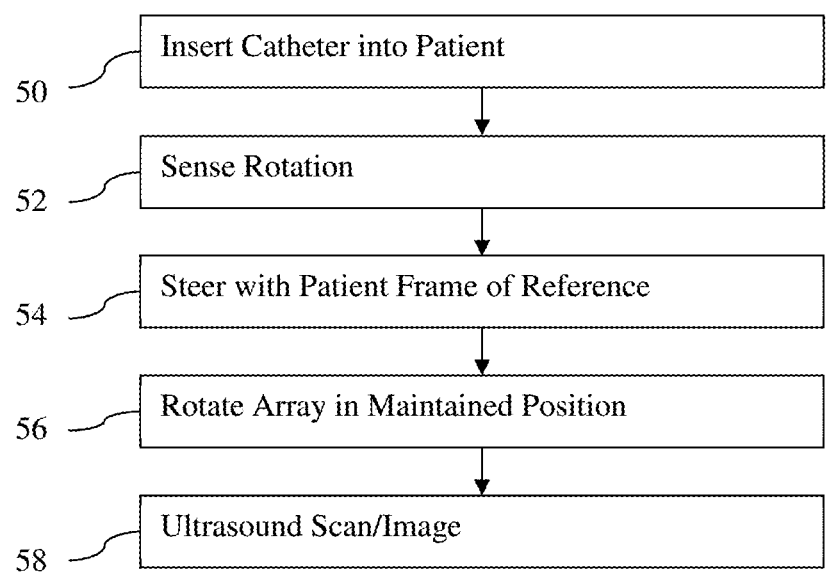
FIG. 5 is a flow chart diagram of one embodiment of a method for steering a catheter in a patient reference frame.

FIG. 5 is a flow chart diagram of one embodiment of a method for steering a catheter. The method includes a method for controlled bending of the catheter. The catheter is steered with respect to a patient frame of reference, so that user input to bend is for bending with respect to anatomy or the patient rather than with respect to the catheter frame of reference. The bending is controlled relative to the patient. This control in bending results in the ability to rotate the catheter around the longitudinal axis while keeping the tip and/or other portion distal to the controlled or steering wire-based bending in position relative to the patient.

The method is implemented by the system and/or ultrasound imaging catheter of FIG. 1, 2, 3, or 4. Alternatively, a different catheter or system is used, such as an ablation catheter.

Additional, different, or fewer acts may be provided. For example, act 50 or other user performed acts are not provided. The acts for steering and maintaining position performed by the controller are performed. As another example, act 58 is not performed where the catheter is not an imaging catheter.

The acts are performed in the order shown or a different order. In the example of FIG. 5, acts 52, 54, and 56 are performed as part of the catheter being manually or automatically rotated, so are performed at a same time or in any sequence. For different embodiments, act 54 is performed prior to act 52 where steering is provided without rotation or prior to rotation.

In act 50, the catheter is inserted into the patient. The catheter is translated along the longitudinal axis. The distal end and tip are inserted into the patient. Any length of catheter may be inserted. As the catheter progresses into the patient, the catheter may bend and/or twist with the vessel into which the catheter is inserted. The user may use steering to guide the catheter, such as applying force to steering wires to bend the catheter to progress in a given direction.

The handle, connected to the rest of the catheter or in a separate control counsel, controls the translation and/or steering for insertion. The control uses manual movement of the handle and/or entry on input devices.

While the catheter is within the patient, the user may rotate the catheter. The catheter rotates about the longitudinal axis. For any bends caused by the vessel path, the catheter flexes to maintain the bend. For any bends caused by steering (i.e., force applied by the steering wires), the catheter resists flexing to bend with the vessel. Where the bend is in a chamber, the catheter does not change the bend. The rotation of the catheter would cause the plane of the bend to rotate. Rather than steering with respect to the catheter and accepting the rotation of the plane of bending, the bend is controlled to alter during rotation so that the plane of the bend is fixed or changes less than 10 degrees (e.g., maintained) relative to the patient.

In act 52, the rotation of the catheter is sensed. The rotation is sensed by a camera, inertial measurement unit, strain gauge, operation of an input to cause rotation, or another sensor.

The rotation of the handle and/or other part of the catheter is sensed. The rotation of the catheter along the longitudinal axis of the catheter is sensed. The sensor may be on or in the handle, in another part of the catheter, or spaced from the catheter and handle.

In act 54, a controller connected with one or more motors, which are connected to steering wires, steers the catheter with respect to the patient reference frame. Rather than steering with respect to the catheter reference frame of the catheter, the controller controls the motors to receive inputs from the user for steering with respect to a current position in the patient. Any bending or straightening by controlled steering is entered as a change relative to the patient. Where rotation is not occurring, the patient and catheter frames of reference may be aligned. Alternatively, the catheter frame of reference is registered with the patient frame of reference so that an input to bend relative to a patient direction (e.g., bend in a coronal plane of the patient or bend towards a valve of the heart) is transformed by the controller to a bend relative to the catheter so that the bend by the catheter in the catheter reference frame is performed to provide the desired bend in the patient frame of reference.

During rotation, the steering is performed to maintain any bending planes of the catheter in positions relative to the patient during rotation of the catheter about a longitudinal axis of the catheter. For imaging, the transducer (e.g., array) is maintained at a same location relative to the patient while the transducer and corresponding field of view are rotated. To maintain the position of the transducer, which is distal to the steering-caused bend, the bend in the catheter is changed. One or more motors, such as in the handle of the catheter, are operated to increase or decrease the forces (e.g., extend or draw in) in the steering wires relative to each other. As the rotation occurs, the bend is altered. The amount of bend (e.g., angle along the longitudinal axis), center of the bend, and/or length of the bend along the catheter is the same or maintained but the angle of the bend about the longitudinal axis changes. Alternatively, any characteristic of the bend may be altered to maintain the position of the tip or transducer, such as to account for interfering anatomy. The bend is altered in one or more ways so that a portion of the catheter distal to the bend remains at a location while also rotating the catheter about the longitudinal axis.

For imaging, the transducer may be at the portion that is maintained in position (i.e., no or limited (e.g., +/−10 degrees) shift in position due to rotation of the bend plane). The controller alters the bend in the catheter caused by steering so that the transducer of the catheter separated from a handle by the bend remains at a location relative to a patient.

In act 56, the transducer may be rotated about the longitudinal axis at the portion, allowing shifting the field of view to image different directions due to the rotation. This rotation of the transducer occurs while the transducer is otherwise maintained in position, at least due to rotation about the longitudinal axis. Motion due to other sources, such as translation along the longitudinal axis, patient motion, and/or unintentional change from the user may cause shift in position while the controller maintains the position with respect to the bend.

The amount of alteration or the change in the steering is based on the sensed rotation. To maintain position, the alteration matches the rotation. The controller responds to the sensed rotation to perform a corresponding alteration in the bend in the catheter.

In act 58, the transducer is used for ultrasound scanning in a field of view. Ultrasound imaging is performed with the transducer. As the field of view shifts due to rotation of the catheter, the field of view and corresponding imaged region shifts. The user may view the surrounding tissue in different directions by rotating the catheter. Since this rotation maintains position of the transducer relative to the patient, the user may more easily review the surrounding tissue in different directions from one position.

In other embodiments, the rotation places a directional aspect of the catheter (e.g., ablation electrode or port) relative to the patient for interaction with the patient. The part of the catheter may be rotated without moving away from the tissue due to the bend plane changing since the control is with respect to the patient frame of reference.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A medical ultrasound system for intra-cardiac echocardiography, the medical ultrasound system comprising:
    an intra-cardiac echocardiography catheter having a tip, a handle, steering wires, and an ultrasound transducer array, wherein the steering wires control a bend at a distal end of the intra-cardiac echocardiography catheter;
    a plurality of motors connected to the steering wires of the intra-cardiac echocardiography catheter;
    a rotation sensor positioned to sense rotation of the handle; and
    a controller configured to establish a patient frame of reference based on registration of a catheter frame of reference with a medical image and to maintain a position of the tip relative to the patient frame of reference during the rotation of the handle by actuation of one or more of the plurality of motors in response to the sensed rotation, wherein the plurality of motors are configured to change relative forces on the steering wires to keep the tip in the position by altering the bend.

2. The medical ultrasound system of claim 1 wherein the ultrasound transducer array comprises a one-dimensional array of transducer elements for scanning a patient within a field of view, the one-dimensional array being on a distal end of the intra-cardiac echocardiography catheter for insertion within the patient.

3. The medical ultrasound system of claim 1 wherein the plurality of motors comprises linear motors.

4. The medical ultrasound system of claim 1 wherein the rotation sensor comprises an inertial measurement unit.

5. The medical ultrasound system of claim 1 wherein the tip rotates as the handle rotates, and wherein the controller is configured to alter the bend in the intra-cardiac echocardiography catheter to maintain the position during the rotation.

6. The medical ultrasound system of claim 1 wherein the rotation causes the ultrasound transducer array and a corresponding field of view to rotate while the position is maintained.

7. The medical ultrasound system of claim 1 further comprising one or more input sensors on the handle, the one or more input sensors configured for steering the intra-cardiac echocardiography catheter from user input, the steering being with respect to the patient frame of reference.

8. The medical ultrasound system of claim 1 further comprising a beamformer configured to scan from the ultrasound transducer array.

9. A method for controlled bending in a catheter, the method comprising:
    sensing, by a sensor, rotation of the catheter along a longitudinal axis of the catheter;
    establishing a patient frame of reference based on registration of a catheter frame of reference with a medical image; and
    altering, by a controller, a bend in the catheter so that a portion of the catheter separated from a handle by the bend remains at a position relative to the patient frame of reference when the handle rotates, the altering of the bend based on the sensed rotation from the sensor.

10. The method of claim 9 wherein the sensing further comprises sensing with an inertial measurement unit in or on the handle of the catheter.

11. The method of claim 9 wherein the altering further comprises operating one or more motors in the handle of the catheter, the one or more motors connected to steering wires of the catheter.

12. The method of claim 9 wherein the altering further comprises maintaining an angle of the bend along the catheter during the rotation and maintaining a location of the bend relative to a patient during the rotation.

13. The method of claim 9 wherein the portion of the catheter includes an acoustic imaging array, and the method further comprising rotating the acoustic imaging array with the rotation, and wherein the altering further comprises altering the bend so that the portion of the catheter remains at the position while also rotating the acoustic imaging array.

14. A method for steering a catheter, the method comprising:
    inserting the catheter into a patient;
    establishing a patient frame of reference based on registration of a catheter frame of reference with a medical image; and
    steering, by a controller and motor, the catheter with respect to the patient frame of reference different than the catheter frame of reference of the catheter, wherein a portion of the catheter separated from a handle by a bend in the catheter remains at a position relative to the patient frame of reference when the handle rotates by altering the bend.

15. The method of claim 14 wherein the steering with respect to the patient frame of reference further comprises maintaining bending planes of the catheter in positions relative to the patient during rotation of the catheter about a longitudinal axis of the catheter.

16. The method of claim 14, further comprising:
    sensing when the handle rotates with an inertial measurement unit.

17. The method of claim 14 further comprising ultrasound scanning a field of view with a transducer in the catheter, wherein the steering further comprises maintaining the transducer at a same location relative to the patient while rotating the transducer and the field of view at the same location.

* * * * *